United States Patent [19]
Colton et al.

[11] 3,954,844
[45] May 4, 1976

[54] (5Z,13E,15S)-15-HYDROXY-11-OXOPROSTA-5,9.13-TRIEN-1-OIC ACID AND ESTERS

[75] Inventors: Frank B. Colton, Evanston; Leland J. Chinn, Morton Grove, both of Ill.

[73] Assignee: G. D. Searle & Co., Chicago, Ill.

[22] Filed: Jan. 3, 1975

[21] Appl. No.: 538,316

[52] U.S. Cl. .................. 260/488 R; 260/410; 260/468 D; 260/514 D; 260/240 R; 424/305; 424/317
[51] Int. Cl.² ............... C07C 61/38; C07C 69/74

[58] Field of Search ......... 260/468 D, 514 D, 488 R

[56] References Cited
UNITED STATES PATENTS
3,862,979   1/1975   Gandolfi et al. ............... 260/514

*Primary Examiner*—Robert Gerstl
*Attorney, Agent, or Firm*—John M. Brown

[57] ABSTRACT

Preparation and the antispasmodic utility of (5Z,13E,-15S)-15-hydroxy-11-oxoprosta-5,9,13-trien-1-oic acid and esters are disclosed.

3 Claims, No Drawings

(5Z,13E,15S)-15-HYDROXY-11-OXOPROSTA-5,9,13-TRIEN-1-OIC ACID AND ESTERS

This invention relates to (5Z,13E,15S)-15-hydroxy-11-oxoprosta-5,9,13-trien-1-oic acid and esters, and to processes for the preparation thereof. More particularly, this invention provides new, useful, and unobvious chemical compounds of the formula

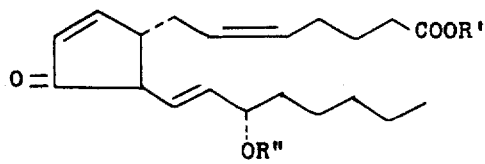

wherein R' represents hydrogen or alkyl and R'' represents hydrogen or 1-oxoalkyl.

Among the alkyls represented by R', lower alkyls are preferred, which is to say methyl, ethyl, propyl, isopropyl, butyl, isobutyl, sec.-butyl, tert.-butyl, pentyl, neopentyl, hexyl, isohexyl, heptyl, and like monovalent, saturated, acyclic, straight- or branched-chain, hydrocarbon groupings of the formula

wherein $n$ represents a positive integer less than 8. The 1-oxoalkyls (heretofore more often termed alkanoyls) represented by R'' are likewise preferably of lower order, i.e., enformulated thus

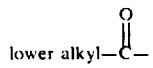

the lower alkyl constituent being defined as above.

The compounds to which this invention relates are useful by reason of their valuable biological properties. In particular, they are antispasmodic.

The antispasmodic utility of the instant compounds is evident from the results of a standardized test for their capacity to antagonize the activity of bradykinin, prostaglandin $E_2$ (PGE$_2$) and/or acetylcholine. The procedure, carried out substantially as described by J. H. Sanner in *Arch. intern. Pharmacodynamie*, 180, 46 (1969), is as follows: A female guinea pig weighing between 200 and 500 g is sacrificed by cervical dislocation, whereupon the ileum is quickly removed and a 2-cm segment thereof mounted in a 5-ml tissue bath containing modified Tyrode solution and adapted to record isotonic contractions. The Tyrode solution, at 37 °C. and constantly bubbled with a mixture of 95% oxygen and 5% carbon dioxide (V/V), consists of 8.046 g of NaCl, 0.200 g of KCl 0.132 g of CaCl$_2$.2H$_2$O, 0.107 g of MgCl$_2$.6H$_2$O, 1.000 g of NaHCO$_3$, 0.058 g of NaH$_2$PO$_4$.H$_2$O, 1.000 g of dextrose, and H$_2$O q.s. 1 l. Doses of bradykinin, PGE$_2$, and acetylcholine necessary to induce approximately equal submaximal contractions are experimentally determined, whereupon two sets of three (one for each agonist at the predetermined dose) such contractions are recorded at 4-minute intervals as controls. The modified Tyrode solution is immediately replaced by a solution or suspension of test compound therein, at 37° and bubbled as before, following which three sets of contractions induced by the three agonists at the predetermined doses are recorded, beginning 4 minutes after the second control recording and continuing at 4-minute intervals thereafter. The first of these three sets serves only to maintain the dosage timing until the tissue is in equilibrium with the test compound. The last two sets are compared with the two control sets, and a compound is considered active vis-a-vis a given agonist if the mean contraction induced thereby in the presence of compound is not more than 25% of the mean control contraction for that agonist. The initial screening dose in this test is ordinarily 30 mcg per ml. At this dose, the product 1E hereinafter reduced the spasmodic effect of bradykinin by 96% and totally blocked the effects of PGE$_2$ and acetylcholine.

Those skilled in the art will recognize that observations of activity in standardized tests for particular biological effects are fundamental to the development of valuable new drugs, both veterinary and human.

Preparation of the alkyl (5Z,13E,15S)-11-oxo-15-(1-oxoalkoxy)prosta-5,9,13-trien-1-oates of this invention proceeds by consecutively contacting a cold methanol solution of (5Z,13E,15S)-15-hydroxy-9-oxoprosta-5,10,13-trien-1-oic acid (prostaglandin A$_2$, commonly designated PGA$_2$) with hydrogen peroxide and aqueous sodium hydroxide, then acidifying; contacting the resultant (5Z,13E,15S)-10$\xi$,11$\xi$-epoxy-15-hydroxy-9-oxoprosta-5,13-dien-1-oic acid with an alkanoic acid anhydride in cold pyridine to esterify the hydroxyl therein; contacting a cold methanol solution of the (5Z,13E,15S)-10$\xi$,11$\xi$-epoxy-9-oxo-15-(1-oxoalkoxy)prosta-5,13-dien-1-oic acid thus obtained with hydrazine hydrate in the presence of a trace of acetic acid, affording (5Z,13E,15S)-11$\xi$-hydroxy-15-(1-oxoalkoxy)prosta-5,9,13-trien-1-oic acid; esterifying the carboxyl therein by contacting an N,N-dimethylformamide solution of the compound with alkyl iodide in the presence of sodium bicarbonate; and oxidizing the hydroxyl in the alkyl (5Z,13E,15S)-11$\xi$-hydroxy-15-(1-oxoalkoxy)prosta-5,9,13-trien-1-oate which eventuates by contacting it in cold acetone with Jones reagent prepared by dissolving 10 parts of chromium trioxide in 20 parts of water and consecutively adding thereto 15 parts of concentrated sulfuric acid and 20 parts of water. Cold ethereal diazomethane can be substituted for the N,N-dimethylformamide, alkyl iodide, and sodium bicarbonate in the penultimate reaction if it is methyl (5Z,13E,15S)-11$\xi$-hydroxy-15-(1-oxoalkoxy)-prosta-5,9,13-trien-1-oate which is desired.

Preparation of tetrahydropyran-2-yl (5Z,13E,15S)-11-oxo-15-tetrahydropyran-2-yloxyprosta-5,9,13-trien-1-oate proceeds by contacting (5Z,13E,15S)-10$\xi$,11$\xi$-epoxy-15-hydroxy-9-oxoprosta-5,13-dien-1-oic acid with 3,4-dihydro-2H-pyran in the presence of p-toluenesulfonic acid, using diethyl ether as the reaction medium; contacting a cold methanol solution of the resultant tetrahydropyran-2-yl (5Z,13E,15S)-10$\xi$,11$\xi$-epoxy-9-oxo-15-tetrahydropyran-2-yloxyprosta-5,13-dien-1-oate with hydrazine hydrate in the presence of a trace of acetic acid; oxidizing the hydroxyl in the tetrahydropyran-2-yl (5Z,13E,15S)-11$\xi$-hydroxy-15-tetrahydropyran-2-yloxyprosta-5,9,13-trien-1-oate thus obtained by contacting in cold acetone with Jones reagent; and cleaving the tetrahydropyranyl group in the tetrahydropyran-2-yl (5Z,13E,15S)-11-oxo-15-tetrahydropyran-2-yloxyprosta-5,9,13-trien-1-oate which eventuates by contacting the compound in methanol with dilute hydrochloric acid.

The alkyl (5Z,13E,15S)-15-hydroxy-11-oxo-5,9,13-trien-1-oates of this invention can be prepared by contacting an N,N-dimethylformamide solution of (5Z,13E,15S)-15-hydroxy-11-oxoprosta-5,9,13-trien-1-oic acid with alkyl halides in the presence of sodium bicarbonate.

The (5Z,13E,15S)-11-oxo-15-(1-oxoalkoxy)prosta-5,9,13-trien-1-oic acids of this invention can be prepared by contacting (5Z,13E,15S)-15-hydroxy-11-oxoprosta-5,9,13-trien-1-oic acid with an alkanoic acid anhydride in cold pyridine.

The following examples describe in detail compounds illustrative of the present invention and methods which have been devised for their preparation. It will be apparent to those skilled in the art that many modifications, both of materials and of methods, may be practiced without departing from the purpose and intent of this disclosure. Throughout the disclosure, temperatures are given in degrees centigrade and relative amounts of materials in parts by weight, except as otherwise noted.

EXAMPLE 1

A. To a solution of 10 parts of PGA$_2$ in 160 parts of methanol at −20° is added, with stirring, 9 parts of hydrogen peroxide and then, slowly, 12 parts of aqueous 12% sodium hydroxide. The resultant mixture is stirred at −20° for 15 minutes, then poured into 100 parts of 5% citric acid. The mixture thus obtained is extracted with ethyl acetate. The extract is washed with water, dried over anhydrous sodium sulfate, and stripped of solvent by vacuum distillation. The oily residue is (5Z,13E,15S)-10ξ,11ξ-epoxy-15-hydroxy-9-oxoprosta-5,13-dien-1-oic acid, which is further purified by chromatography on silica gel, using 30% ethyl acetate in benzene both to pack the gel and develop the chromatogram. The purified product can be represented by the formula

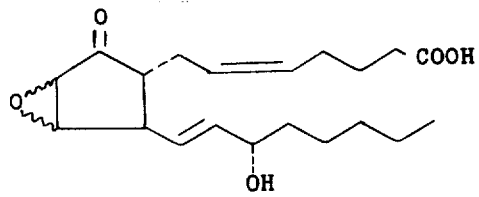

in which the wavy lines indicate that the configuration of the epoxy grouping is various.

B. To a solution of 1 part of (5Z,13E,15S)-10ξ,11ξ-epoxy-15-hydroxy-9-oxoprosta-5,13-dien-1-oic acid in 30 parts of pyridine at 5° is added 10 parts of acetic anhydride. The resultant mixture is allowed to stand at 5° for 18 hours, whereupon it is poured into 10 volumes of water. The mixture thus obtained is allowed to stand for 1 hour, then extracted with ethyl acetate. The extract is washed with water, dried over anhydrous sodium sulfate, and stripped of solvent by vacuum distillation. The residual red oil is taken up in benzene; and the benzene solution is chromatographed on silica gel, using benzene and mixtures thereof with increasing amounts of ethyl acetate as developing solvents. From an eluate comprising 20% ethyl acetate in benzene, on evaporation of solvent, (5Z,13E,15S)-15-acetoxy-10ξ,11ξ-epoxy-9-oxoprosta-5,13-dien-1-oic acid is obtained as a pale yellow oil.

C. To a solution of 30 parts of (5Z,13E,15S)-15-acetyloxy-10ξ,11ξ-epoxy-9-oxoprosta-5,13-dien-1-oic acid in 1200 parts of methanol at 5° is added a solution of 12 parts of 100% hydrazine hydrate in 96 parts of methanol followed by a solution of 1 part of acetic acid in 5 parts of methanol. The resultant mixture is stirred at 5° for 30 minutes, then acidified with aqueous 2% citric acid. The mixture thus obtained is extracted with dichloromethane. The extract is washed with water, dried over anhydrous sodium sulfate, and stripped of solvent by vacuum distillation. The residual red oil is taken up in benzene; and the benzene solution is chromatographed on silica gel, using benzene and mixtures thereof with increasing amounts of ethyl acetate as developing solvents. From an eluate comprising 20% ethyl acetate in benzene, on evaporation of solvent, (5Z,13E,15S)-15-acetyloxy-11ξ-hydroxyprosta-5,9,13-trien-1-oic acid is obtained as a colorless oil which gradually darkens upon standing.

D. To a solution of 8 parts of (5Z,13E,15S)-15-acetyloxy-11ξ-hydroxyprosta-5,9,13-trien-1-oic acid in 175 parts of diethyl ether is added an ethereal solution of diazomethane prepared from 30 parts of N-nitrosomethylurea, 90 parts of aqueous 40% potassium hydroxide, and 210 parts of diethyl ether as described in Org. Syn., 15, 4 (1935). The resultant mixture is allowed to stand at 5° for 30 minutes, whereupon 2 parts of acetic acid is introduced and the mixture thus obtained extracted with diethyl ether. The extract is washed with water, dried over anhydrous sodium sulfate, and stripped of solvent by vacuum distillation. The residual red oil is taken up in benzene; and the benzene solution is chromatographed on silica gel, using benzene and mixtures thereof with increasing amounts of ethyl acetate as developing solvents. From an eluate comprising 30% ethyl acetate in benzene, on evaporation of solvent, methyl (5Z,13E,15S)-15-acetyloxy-11ξ-hydroxyprosta-5,9,13-trien-1-oate is obtained as a pale yellow oil.

E. To a solution of 26 parts of methyl (5Z,13E,15S)-15-acetyloxy-11ξ-hydroxyprosta-5,9,13-trien-1-oate in 200 parts of acetone at −10° is added 100 parts of Jones reagent. The resultant mixture is stirred at −10° for 7 minutes, then diluted with 10 volumes of water. The mixture thus obtained is extracted with dichloromethane. The extract is washed with water, dried over anhydrous sodium sulfate, and stripped of solvent by vacuum distillation. The oily residue is taken up in benzene; and the benzene solution is chromatographed on silica gel, using benzene and mixtures thereof with increasing amounts of ethyl acetate as developing solvent. From an eluate comprising 5% ethyl acetate in benzene, on evaporation of solvent, methyl (5Z,13E,15S)-15-acetyloxy-11-oxoprosta-5,9,13-trien-1-oate is obtained as a pale yellow oil. The product has the formula

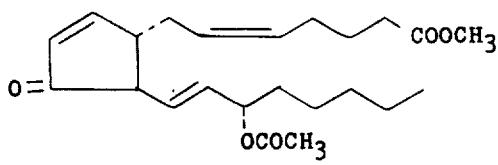

EXAMPLE 2

A. A solution of 5 parts of (5Z,13E,15S)-10ξ,11ξ-epoxy-15-hydroxy-9-oxoprosta-5,13-dien-1-oic acid, 10 parts of 3,4-dihydro-3H-pyran, and 1 part of p-toluenesulfonic acid monohydrate in 35 parts of diethyl ether is allowed to stand at room temperatures for 15 hours, then poured into 100 parts of aqueous 5% sodium bicarbonate. The ethereal phase is separated, washed with water, dried over anhydrous sodium sulfate, and stripped of solvent by vacuum distillation. The residue is tetrahydropyran-2-yl (5Z,13E,15S)-10ξ,11ξ-epoxy-9-oxo-15-tetrahydropyran-2-yloxyprosta-5,13-dien-1-oate.

B. Substitution of 30 parts of tetrahydropyran-2-yl (5Z,13E,15S)-10ξ,11ξ-epoxy-9-oxo-15-tetrahydropyran-2-yloxyprosta-5,13-dien-1-oate for the (5Z,13E,15S)-15-acetyloxy-10ξ,11ξ-epoxy-9-oxoprosta-5,13-dien-1-oic acid called for in Example 1C affords, by the procedure there detailed, tetrahydropyran-2-yl (5Z,13E,15S)-11ξ-hydroxy-15-tetrahydropyran-2-yloxyprosta-5,9,13-trien-1-oate.

C. Substitution of 20 parts of tetrahydropyran-2-yl (5Z,13E,15S)-11ξ-hydroxy-15-tetrahydropyran-2-yloxyprosta-5,9,13-trien-1-oate for the methyl (5Z,13E,15S)-15-acetyloxy-11ξ-hydroxyprosta-5,9,13-trien-1-oate called for in Example 1E affords, by the procedure there detailed, tetrahydropyran-2-yl (5Z,13E,15S)-11-oxo-15-tetrahydropyran-2-yloxyprosta-5,9,13-trien-1-oate.

D. A mixture of 1 part of tetrahydropyran-2-yl (5Z,13E,15S)-11-oxo-15-tetrahydropyran-2-yloxyprosta-5,9,13-trien-1-oate, 7 parts of 10% hydrochloric acid, and 560 parts of methanol is allowed to stand at room temperature for 1 hour, whereupon it is extracted with dichlormethane. The extract is washed with water, dried over anhydrous sodium sulfate, and stripped of solvent by vacuum distillation. The residue is (5Z,13E,15S)-15-hydroxy-11-oxoprosta-5,9,13-trien-1-oic acid.

EXAMPLE 3 a. Substitution of 13 parts of propionic acid anhydride for the acetic anhydride called for in Example 1B affords, by the procedure there detailed, (5Z,13E,15S)-10ξ,11ξ-epoxy-9-oxo-15-(1-oxopropoxy)prosta-5,13-dien-1-oic acid.

B. Substitution of 30 parts of (5Z,13E,15S)-10ξ,11ξ-epoxy-15-(1-oxopropoxy)prosta-5,13-dien-1-oic acid for the (5Z,13E,15S)-15-acetyloxy-10ξ,11ξ-epoxy-9-oxoprosta-5,13-dien-1-oic acid called for in Example 1C affords, by the procedure there detailed, (5Z,13E,15S)-11ξ-hydroxy-15-(1-oxopropoxy)prosta-5,9,13-trien-1-oic acid.

C. A mixture of 18 parts of (5Z,13E,15S)-11ξ-hydroxy-15-(1-oxopropoxy)prosta-5,9,13-trien-1-oic acid, 7 parts of ethyl iodide, 4 parts of sodium bicarbonate, and 250 parts of N,N-dimethylformamide is stirred at room temperatures for 15 hours, then diluted with 2500 parts of water. The resultant mixture is extracted with ether. The extract is washed with water, dried over anhydrous sodium sulfate, and stripped of solvent by vacuum distillation. The residue is ethyl (5Z,13E,15S)-11ξ-hydroxy-15-(1-oxopropoxy)prosta-5,9,13-trien-1-oate.

D. Substitution of 30 parts of ethyl (5Z,13E,15S)-11ξ-hydroxy-15-(1-oxopropoxy)prosta-5,9,13-trien-1-oate for the methyl (5Z,13E,15S)-15-acetyloxy-11ξ-hydroxyprosta-5,9,13-trien-1-oate called for in Example 1E affords, by the procedure there detailed, ethyl (5Z,13E,15S)-11-oxo-15-(1-oxopropoxy)prosta-5,9,13trien-1-oate.

EXAMPLE 4

A mixture of 15 parts of (5Z,13E,15S)-15-hydroxy-11-oxoprosta-5,9,13-trien-1-oic acid, 7 parts of iodomethane, 4 parts of sodium bicarbonate, and 250 parts of N,N-dimethylformamide is stirred at room temperature for 15 hours. The resultant mixture is diluted with 2500 parts of water. The mixture thus obtained is extracted with ether. The extract is washed with water, dried over anhydrous sodium sulfate, and stripped of solvent by vacuum distillation. The residue is methyl (5Z,13E,15S)-15-hydroxy-11-oxoprosta-5,9,13-trien-1-oate.

EXAMPLE 5

Substitution of 8 parts of 2-iodopropane for the iodomethane called for in Example 4 affords, by the procedure there detailed, 1-methylethyl (5Z,13E,15S)-15-hydroxy-11-oxoprosta-5,9,13-trien-1-oate.

EXAMPLE 6

Substitution of 1 part of (5Z,13E,15S)-15-hydroxy-11-oxoprosta-5,9,13-trien-1-oic acid for the (5Z,13E,15S)-10ξ,11ξ-epoxy-15-hydroxy-9-oxoprosta-5,13-dien-1-oic acid called for in Example 1B affords, by the procedure there detailed, (5Z,13E,15S)-15-acetyloxy-11-oxoprosta-5,9,13-trien-1-oic acid.

What is claimed is:

1. A compound of the formula

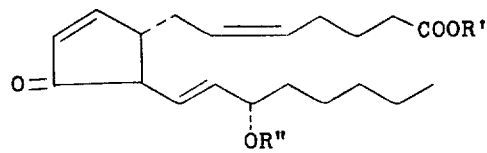

wherein R' represents hydrogen or lower alkyl and R'' represents hydrogen or 1-oxo(lower alkyl).

2. A compound according to claim 1 which is methyl (5Z,13E,15S)-15-acetyloxy-11-oxoprosta-5,9,13-trien-1-oate.

3. A compound according to claim 1 which is (5Z,13E,15S)-15-hydroxy-11-oxoprosta-5,9,13-trien-1-oic acid.

* * * * *